United States Patent Office

Plant Pat. 3,681

Patented Feb. 4, 1975

3,681
ST. AUGUSTINEGRASS

Jake T. Gruis, Apopka, and Terrance P. Riordan, Altamonte Springs, Fla., assignors to The O. M. Scott & Sons Company, Marysville, Ohio Filed Oct. 2, 1973, Ser. No. 402,717
Int. Cl. A01h 5/12
U.S. Cl. Plt.—88 1 Claim

ABSTRACT OF THE DISCLOSURE

A perennial St. Augustinegrass having a moderate olive green color, a very dwarf growth habit, a fine texture, a reduction in flowering shoots, and a very good gray leafspot resistance. This genotype possesses moderately vigorous stolon growth and is propagated vegetatively.

SUMMARY OF THE VARIETY

This invention relates to a new and distinct perennial St. Augustinegrass selected from a series of $F_2$ generation selfs of a purple stigma diploid parent (Ea611081). This purple stigma self was labeled 73176 and propagated vegetatively by stolons to provide planting stock for studying performance and comparison to present commercial varieties.

Genotype 73176 has a fine texture, a reduction in flowering shoots, and very good gray leafspot (*Piricularia grisea*) resistance. It has also the most dwarf growth habit of any St. Augustinegrass yet described, and it can, in fact accordingly be distinguished from other St. Augustines by this characteristic.

BRIEF DESCRIPTION OF THE ILLUSTRATIONS

DETAILED DESCRIPTION OF THE VARIETY

Figure 1:
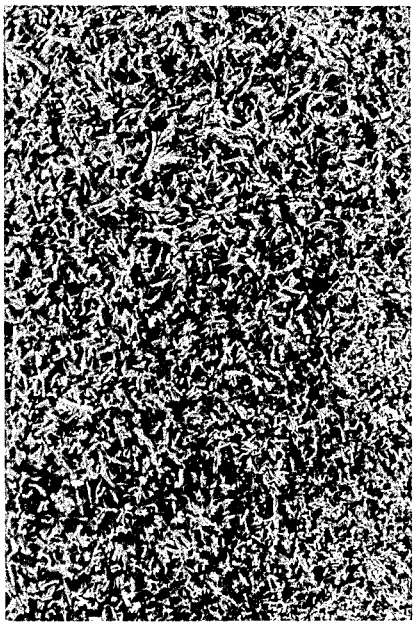
FIG. 1 is a photograph of 73176 St. Augustine turf showing generally the characteristics of this new grass.
Figure 2:
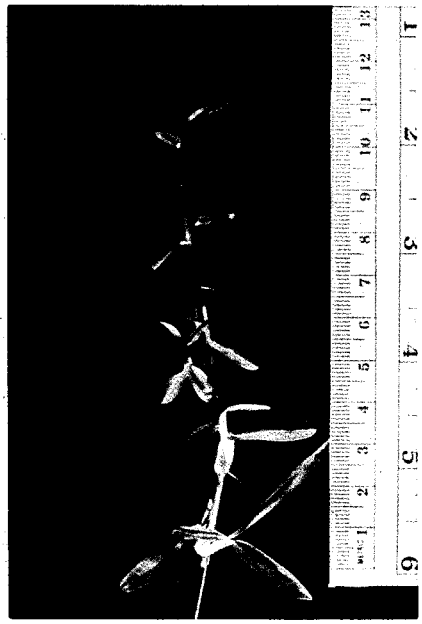
FIG. 2 shows the leaves and stem of a 73176 St. Augustinegrass plant.
Figure 3:
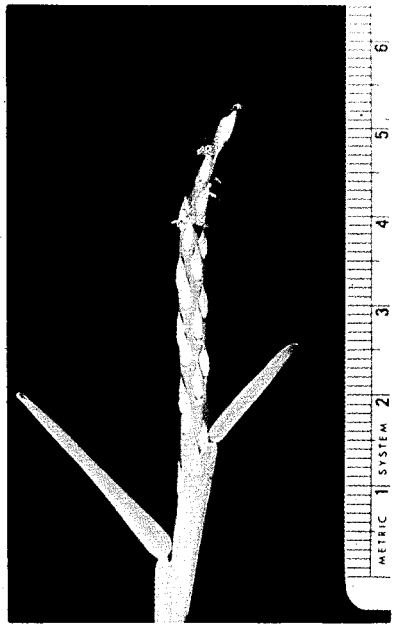
FIG. 3 shows a spike of a 73176 St. Augustinegrass plant.
Figure 4:
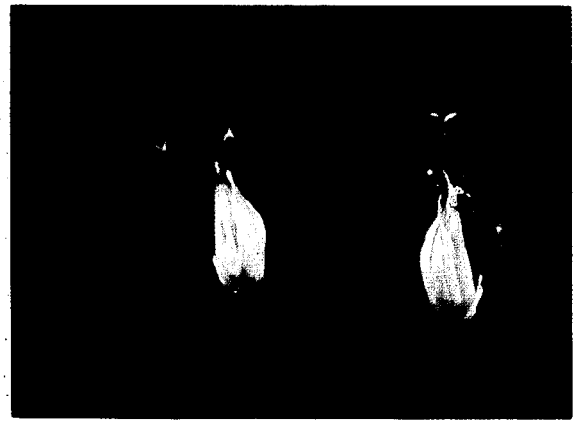
FIG. 4 shows florets of a 73176 St. Augustinegrass plant.

Genotype 73176 possesses a moderate olive green color (7.5 GY 4/4) [1] and is characterized by compressed and branched culms. The leaf blades average 33.4 mm. long and average 5.86 mm. wide, with the average internode length 10.8 mm. Gentoype 73176 has a purple stigma color and an unreduced chromosome number of 18.

Total soluble salts as measured by micromhos/cm. specific conductance using a Beckman Solu-Bridge has given a reliable differentiation among some genotypes. The average reading for a 73176 stem section was a very low 107.3 micromhos/cm. The chromosome numbers, stigma colors, morphological measurements, and specific conductance measurements of 73176 and other St. Augustinegrasses are compared in Tables 1, 2, and 3.

[1] Munsell color designation obtained using a Nickerson color fan. The designated color is of plant material grown in the greenhouse. The color is subject to variation depending upon the environmental conditions under which the grass is grown.

TABLE 1

Chromosome numbers and stigma colors of 73176 and other St. Augustinegrasses

| Selection/variety | Chromosome number (unreduced) [1] | Stigma color |
|---|---|---|
| 73176 | 18 | Purple. |
| Ea611081 | 18 | Do. |
| Floratine | 27 | Do. |
| Bitter Blue | 27 | Do. |
| Texas Common | 18 | White. |

[1] Chromosome number determinations made on pollen mother cells.

TABLE 2

Comparative leaf blade length, width, and internode length for 73176 and other St. Augustinegrasses

| Selection/variety | Leaf blade Length (mm.) [1] | Leaf blade Width (mm.) [2] | Internode length (mm.) [3] |
|---|---|---|---|
| 73176 | 33.4±7.3 | 5.86±1.09 | 10.8±2.2 |
| Ea611081 | 78.4±33.3 | 7.12±1.38 | 36.0±7.4 |
| Floratine | 82.8±25.9 | 7.81±2.46 | 36.3±7.3 |
| Bitter Blue | 105.2±31.8 | 8.55±1.25 | 38.3±8.7 |
| Texas Common | 45.0±16.8 | 6.48±0.85 | 34.0±4.2 |
| LSD 5% | 12.1 | .71 | 4.0 |

[1] All plant material grown unclipped in greenhouse.
[2] Measurements recorded 15 millimeters above leaf collar.
[3] Measurements recorded between third and fourth internodes.

TABLE 3

Specific conductance measurements of 73176 and other St. Augustinegrasses

| Selection/variety: | Specific conductance (Micromhos/cm.) [1] |
|---|---|
| 73176 | 107.3 |
| Ea611081 | 132.3 |
| Bitter Blue | 190.2 |
| Texas Common | 122.8 |

In addition to the foregoing, field observations at both the Apopka, Fla., and Katy, Tex., field stations demonstrate the very dwarf characteristic of 73176 when compared to other St. Augustinegrasses. Clipping yield studies carried out during the summer period of active growth can also be relied upon to distinguish 73176 from other St. Augustines. This information is given in Tables 4, 5 and 6.

TABLE 4

Comparative growth habit averages for 73176 and other St. Augustinegrasses at Apopka, Florida, and Katy, Texas

| Selection/variety | Growth habit [1] Florida 1971 | Texas 1971 | Florida 1972 |
|---|---|---|---|
| 73176 | 2.4 | 2.5 | 1.6 |
| Ea611081 | 3.4 | 4.0 | 3.2 |
| Bitter Blue | 4.4 | 4.5 | 3.7 |
| Texas Common | | 4.5 | |
| LSD 5% | | | .2 |

[1] Rating 1=low growing, 5-upright growing.

TABLE 5

Comparative texture average for 73176 and other St. Augustinegrasses at Apopka, Florida and Katy, Texas

| Selection/variety | Texture [1] Florida 1971 | Texas 1971 | Florida 1972 |
|---|---|---|---|
| 73176 | 2.9 | 2.5 | 3.1 |
| Ea611081 | 1.7 | 2.0 | 2.3 |
| Bitter Blue | 1.4 | 1.5 | 2.0 |
| Texas Common | | 1.1 | |
| LSD 5% | | | .2 |

[1] Rating 4=fine texture, 1=coarse.

TABLE 6

Fresh weights of clippings removed from plots of 73176 and other St. Augustinegrasses

| Selection/variety | Fresh weights (gms/.48 m. x 1.52 m. plot) July | August | September |
|---|---|---|---|
| 73176 | 3.0±1.7 | 6.0±3.6 | 7.7±2.9 |
| Ea611081 | 36.7±12.9 | 74.0±12.5 | 45.0±8.2 |
| Bitter Blue | 22.3±9.9 | 43.7±15.3 | 29.7±4.9 |
| LSD 5% | 16.6 | 21.8 | 11.0 |

Another important characteristic allowing differentiation of 73176 from other St. Augustinegrasses is the reduction in flowering shoots. Since 73176 is propagated vegetatively by propagules there is no need for the unattractive racemes and any reduction in these flowering shoots would be an obvious advantage. This reduction is shown in Table 7.

TABLE 7

Comparative ratings of average flowering shoot production in 73176 and other St. Augustinegrasses at Apopka, Florida and Katy, Texas

| Selection/variety | Average flowering shoot production[1] | |
|---|---|---|
| | Texas 9/17/71 | Florida 6/15/72 |
| 73176 | 0 | .7 |
| Ea611081 | 0 | 2.0 |
| Bitter Blue | 0 | 1.3 |
| Texas Common | 3 | |
| LSD 5% | | 1.0 |

[1] Rating 0=no flowering shoot production, 5=heavy flowering shoot production.

Table 8 shows the high level of gray leafspots (*Piricularia grisea*) resistance of 6–71–37 when compared to other St. Augustinegrasses in both Texas and Florida. A high level of resistance is shown throughout the year.

TABLE 8

Comparative gray-leafspot (*Piricutaria grisea*) resistance of 73176 and other St. Augustinegrasses at Apopka, Florida and Katy, Texas

| | Percent gray leafspot | | | | | |
|---|---|---|---|---|---|---|
| | Florid : | | | Texas | | |
| | 6/28/71 | 4/31/71 | 6/29/71 | 7/31/71 | 9/2/71 | 9/17/71 |
| 73176 | 20 | 10 | 10 | 20 | 5 | 0 |
| Ea611081 | 20 | 10 | 20 | 30 | 10 | 30 |
| Bitter Blue | 40 | 90 | 20 | 10 | 10 | 20 |
| Texas Common | | 100 | 10 | 60 | 30 | 20 |

Cold hardiness also allows differentiation of 73176 from other commercial St. Augustinegrasses. Genotype 73176 will not withstand below zero centigrade temperatures as well as the more vigorous varieties, though some added protection is available at near zero temperatures through a reduction in the thatch layer.

The distinguishing cold hardiness data is shown in Table 9.

TABLE 9

Comparative cold damage from below zero (centigrade) temperatures of 73176 and other St. Augustinegrasses in Apopka, Florida and Katy, Texas

| Selection/variety | Percent cold damage[1] | | |
|---|---|---|---|
| | | Florida 1973 | |
| | Texas 1972 | Test—A[2] | Test—B[3] |
| 73176 | 99 | 40 | 35.0 |
| Ea611081 | 99 | 15 | 50.0 |
| Bitter Blue | 20 | 5 | 52.5 |
| Texas Common | 0 | | |

[1] Cold damage as measured by percent stolons killed.
[2] Test—A, Two year old sod.
[3] Test—B, One year old sod.

Table 10 compares the morphological characteristics of spikelets of 73176 with other St. Augustinegrasses.

TABLE 10

Comparative morphological characteristics of spikelets on 73176 and other St. Augustinegrasses

| Selection/variety | Length of— | | | |
|---|---|---|---|---|
| | First glume (mm.)[1] | Second glume (mm.) | Lemma (mm.) | Palea (mm.) |
| 73176 | 1.04±.10 | 3.96±.14 | 3.68±.13 | 3.29±.15 |
| Ea611081 | 1.08±.08 | 3.99±.14 | 3.58±.21 | 3.24±.18 |
| Texas Common | .99±.11 | 3.99±.18 | 3.67±.21 | 3.20±.12 |
| LSD 5% | .07 | .06 | .12 | .09 |

[1] Measurements recorded in millimeters using 12.5× magnification.

What is claimed and desired to be secured by Letters Patent is:

1. A St. Augustinegrass, substantially as herein illustrated and described.

No references cited.

ROBERT E. BAGWILL, Primary Examiner